United States Patent [19]

Collins

[11] 4,118,015
[45] Oct. 3, 1978

[54] DEVICE FOR SAMPLING MOLTEN METAL

[76] Inventor: William J. Collins, 7005 Madison St., Merrillville, Ind. 46410

[21] Appl. No.: 786,664

[22] Filed: Apr. 11, 1977

Related U.S. Application Data

[63] Continuation of Ser. No. 639,468, Dec. 10, 1975, abandoned.

[51] Int. Cl.² ............................................. G01N 1/10
[52] U.S. Cl. ..................................... 266/44; 164/98; 266/287; 73/425.4 R
[58] Field of Search .................... 75/200; 148/126; 164/98; 266/287, 44; 73/425.4

[56] References Cited

U.S. PATENT DOCUMENTS

| | | | |
|---|---|---|---|
| 3,415,124 | 12/1968 | Collins | 73/425.4 R |
| 3,796,566 | 3/1974 | Brondyke et al. | 75/200 X |
| 3,900,940 | 8/1975 | Gebherd, Jr. | 29/420 |
| 3,948,309 | 4/1976 | Cordone et al. | 165/98 |

Primary Examiner—Roy Lake

[57] ABSTRACT

The invention involves a device for obtaining a sample of molten metal for analysis. The device comprises wall structure which is constructed from powdered metal or material to define what may be termed a chamber or cavity for receiving a sample of molten metal. This wall structure is porous and the primary objective of the subject invention is to condition or treat the wall structure in such a way that the porosity of the structure is materially reduced, the purpose of which is to prevent the sample obtained from sticking or becoming cohesive with the inner surfaces of the structure defining the chamber.

13 Claims, 7 Drawing Figures

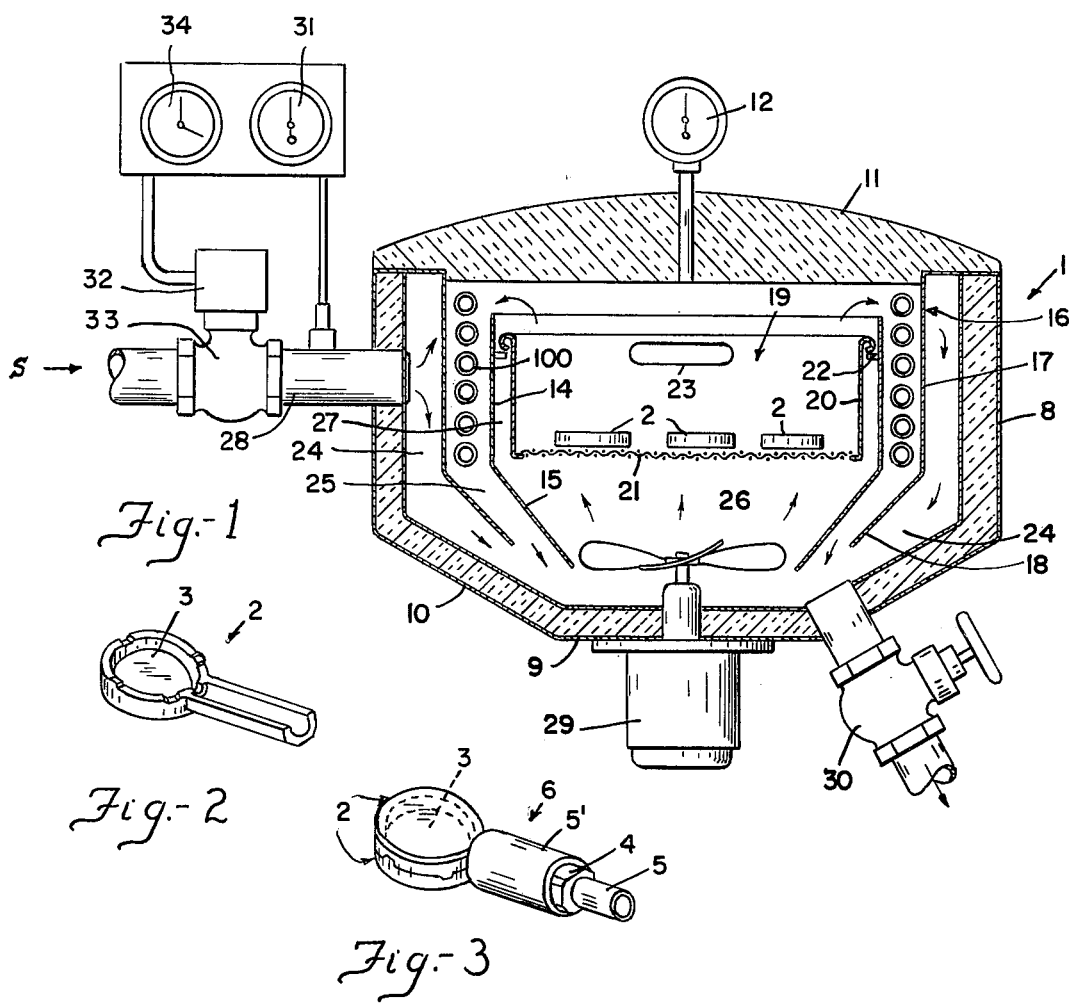
Fig.-1
Fig.-2
Fig.-3
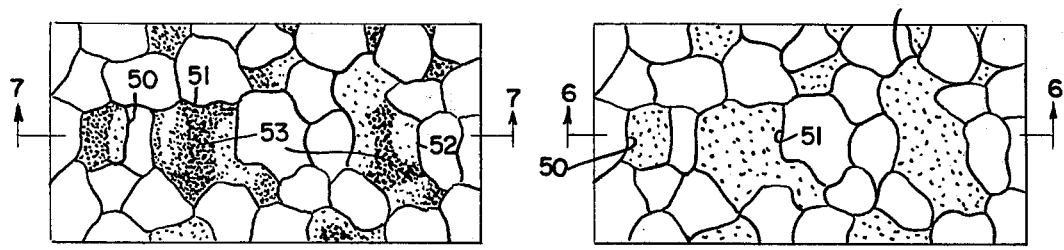
Fig.-5  Fig.-4
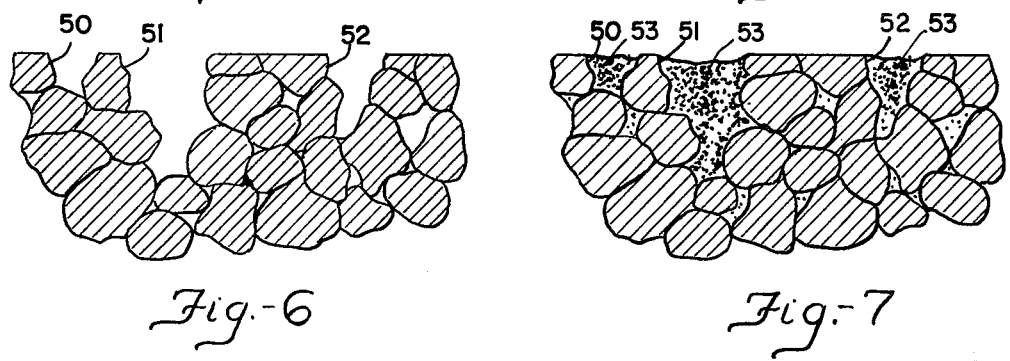
Fig.-6  Fig.-7

DEVICE FOR SAMPLING MOLTEN METAL

The subject Application is a continuation of my earlier application Ser. No. 639,468 filed Dec. 10, 1975 now abandoned.

BACKGROUND OF THE INVENTION

Various devices have heretofore been employed to obtain samples of molten metal and one of these devices is disclosed in my U.S. Pat. No. 3,415,124 which issued on Dec. 10, 1968. In this patent and others there is disclosed, among other things, a device having wall structure, preferably in the form of a pair of mating half sections or portions which are constructed of molded powdered metal and are formed with recesses and channel portions which when correctly assembled define a chamber for receiving the metal and a tubular formation through which the metal flows into the chamber.

The wall structure of such sections has a predetermined porosity and as a result the inner surfaces defining the chamber are provided with minute voids, pockets, or pores and infitisimal portions of the molten metal flow into the pores and cause the solidified sample to adhere or stick to the inner surfaces of the chamber thereby making it difficult to release the sample. Such cohesiveness also leaves the sample with irregular or imperfect surfaces for analysis.

OBJECTIVES OF THE INVENTION

In view of the foregoing, the primary objective of the subject invention is to provide means for conditioning or treating the wall structure of the device in a manner whereby to appreciably reduce its porosity or otherwise appreciably increase its density, the purpose of which is to prevent sticking or cohesion of a sample in the chamber and thereby readily promote its release. Such conditioning also serves to improve the character or smoothness of the external surfaces of the sample in order to facilitate and obtain a more efficient analysis of the metal.

The most efficient way for accomplishing the above objective preferably comprises a method which subjects the half sections or wall structure to a bath of high temperature steam for a predetermined period of time to substantially render the wall structure more dense by substantially eliminating the pores or voids and smoothing out the inner surfaces defining the chamber of the device, and thereby facilitate release of a solid metal sample from the chamber.

An important object of the invention is to obtain a sample which is superior to one obtained in a chamber which has not been treated by such a method, because at least certain of the internal surfaces of the sample are rendered substantially smooth to facilitate analysis of the sample as compared to a sample having pitted or interrupted external surfaces.

It is recognized that steam treatment is utilized in the industry to harden the external surfaces of such items as structural steel, high speed cutting tools, molded rubber, etc. but insofar as is presently known no one prior to the advent of the subject invention has ever utilized such treatment with respect to treating or conditioning the inner surfaces of a chamber of a device for obtaining a sample of molten metal.

Attention is also directed to the fact that the steel industry has recognized the affinity between steel sticking to large iron molds or other receptacles into which the iron or steel is poured and that such molds or receptacles are usually coated with graphite wash to present a more uniform skin condition or smoother surface to minimize the adherence of the metal to the receptacle.

The invention also offers advantages with respect to economical and practical aspects as will become apparent after the description hereinafter set forth is considered in conjunction with the drawings annexed hereto.

DRAWINGS

In the drawings:

FIG. 1 is a schematic view of a furnace or equipment which may be utilized to produce the results intended by the invention;

FIG. 2 is perspective view of one of a pair of half-sections of the device depicted in FIG. 3;

FIG. 3 is a perspective view of a device for obtaining a sample of hot liquid such as molten metal;

FIG. 4 is intended to represent an untreated internal face surface of a chamber of the device;

FIG. 5 is intended to represent a treated internal face surface of a chamber;

FIG. 6 is a section taken substantially on line 6—6 of FIG. 4; and

FIG. 7 is a section taken substantially line 7—7 of FIG. 5.

DESCRIPTION

Referring to FIG. 1 of the drawing there is disclosed a furnace or equipment, generally designated 1, for treating wall structure made from powdered metal. The wall structure to be treated is disclosed in FIGS. 2 and 3 and preferably comprises a pair of half-sections, generally designated 2, which are provided with recesses and channel-like extensions which respectively define a chamber 3 and a tubular formation 4. A tube 5 of refractory material is preferably secured in the formation 4 for initially receiving molten metal for flow through the tubular formation into the chamber for solidification. A sleeve 5′ preferably constructed of pasteboard surrounds the formation 4 whereby to facilitate holding the sections and the tube 5 operatively assembled. The half-sections, tube, and sleeve constitute a device generally designated 6 for obtaining a sample from a stream of molten metal but it is to be distinctly understood that the subject invention is also applicable to a device adapted for disposition in a substantially horizontal stream of molten metal or for immersion.

The half-sections 2 of the device may be treated or conditioned in any conventional furnace or equipment suitable for the purpose and the furnace disclosed is one which may be employed to achieve the objectives of the invention.

More particularly, the furnace shown is generally cylindrical in shape and comprises an insulated housing having a cylindrical side wall 8, a bottom wall 9, and an inclined wall 10 joining the walls 8 and 9. The housing is provided with a cover 11 which carries a steam gauge 12 and with an inner member having a cylindrical wall 14 disposed in a concentrically spaced relation to the side wall 8 of the housing and a truncated conical or tapered cylindrical portion 15 which is disposed in an inclined spaced relation to the inclined wall 10.

The housing is also provided with a member generally designated 16 having a cylindrical wall 17 which is disposed in concentrically spaced relation between the side wall 8 of the housing and the cylindrical wall 14 of member 13 and with a tapered cylindrical portion 18 concentrically disposed between the portion 15 of the inner member 13 and wall 10 of the housing. The member 16 may be supported by the housing as shown and the member 13 may be mounted in and to the member 16 by brackets (not shown).

A container or tray generally designated 19 is disposed in the inner member and includes a cylindrical portion 20 disposed in concentrically spaced relation to the wall 14 of member 13 and a bottom wall 21 which is preferably in the form of a coarse screen. The container 19 is supported on abutments on the wall 14 of the member 13 and is provided with openings 23 through which the hands of an operator or a lifter (now shown) may be inserted to facilitate placement and removal of the container. Some of many half-sections 2 are shown as being disposed in the container on its bottom wall 21.

Attention is directed to the fact that the organization or relationship of the components is preferably such that a chamber 24 is formed between the housing and member 16, a chamber 25 between members 13 and 16, a center chamber 26 below the container 19, and a chamber 27 between the container 19 and 13.

The housing is also provided with an inlet pipe 28 which communicatively connects the chamber 24 with a main line supply S of steam, and since the chamber 24 is communicatively connected with the chambers 25, 26 and 27 steam under pressure may be caused to flow and/or circulate through the chambers for the purpose of subjecting the half-sections 2 to steam. It should be noted that steam will flow about and through the container 19 and that the flow is aided or supplemented by a fan unit 29 secured to the bottom wall 9 of the housing. If so desired, additional heat may be imparted to the half-sections by a ring or annulus of steam pipes 100 which may be disposed between the wall portions 14 and 17 and may be connected to the source S or to a second source of steam, or, if so desired, additional heat may be supplied with an electric grid in lieu of the pipes 100.

It should be further noted that the wall 10 of the housing is provided with a valved outlet 30 and that the inlet pipe 28 is provided with a temperature gauge 31 which may be utilized in conjunction with the gauge 12 and a control 32 is carried by a union 33 on the inlet pipe 28. The control 32 is preferably tied in with a time clock 34 which can be set to subject the half-sections 2 to steam for a predetermined period of time. When the pressure or temperature of the steam has been correctly established by the gauges 12 and 31 the clock can be set for the time that the half-sections are to be treated or conditioned.

If so desired, the valved outlet 30 may be operatively connected to the control 32 so that the outlet will open to release the pressure only after the sections have been treated for the period set by the time clock 34.

As alluded to above, any furnace suitable for the purpose may be employed to heat the half-sections to a predetermined temperature for a predetermined period of time which is sufficient to appreciably reduce the porosity of the inner surfaces and render them substantially smooth, as compared to untreated inner surfaces.

The furnace shown is intended to heat the sections at a temperature within a range of between 550° and 1300° for a period of time between four to six hours. The furnace with the assistance of the fan unit 29 circulates the steam heat into and about the sections in a uniform and efficient manner to reduce the porosity of the chamber surfaces by causing iron oxide to substantially fill the pores, and this factor is exemplified in FIGS. 5 and 7 of the drawings.

More particularly, FIG. 4 is intended to represent a microscopic face view of an untreated inner surface of a chamber of a half section and FIG. 6, a section taken on line 6—6, to magnify infinitesimal pores, such as 50, 51, and 52 of various shapes, as compared to a treated surface as depicted in FIG. 5 and the substantial filling or sealing of the pores 50, 51, and 52 by iron oxide 53 and smoothing out of the surface as shown in FIG. 7.

The use of the word "powdered" material is intended to include any metal material which is comminuted, pulverized or granulated or has an inner surface provided with pores, which without filling, would cause metal to stick thereto.

Having thus described my invention, it is obvious that various modifications may be made in the same without departing from the spirit of the invention, and, therefore I do not wish to be understood as limiting myself to the exact forms, constructions, arrangements, and combinations of parts herein shown and described.

I claim:

1. A method which comprises steam treating internal porous surfaces of a chamber constructed of molded powdered metal for receiving a sample of molten metal whereby to substantially cause filling of said pores to minimize sticking of a sample obtained in said chamber.

2. In a device comprising wall structure molded from powdered metal material and provided with inner surfaces defining a chamber for receiving a sample of molten metal and said inner surfaces have a multitude of infinitesimal pores, the improvement which comprises steam treating said surfaces whereby to substantially fill said pores to substantially prevent a sample obtained from sticking to said inner surfaces.

3. In a device comprising wall structure molded from a powdered metal material to provide inner surfaces defining a chamber for receiving a sample of molten metal and said inner surfaces having a multitude of infinitesimal pores, the improvement which comprises steam treating the material to substantially seal said pores and render said surfaces substantially smooth whereby to substantially prevent a sample obtained from adhering to said inner surfaces.

4. A device for obtaining a sample of molten metal, said device comprising a pair of sections molded from a powdered metal material to provide enlarged recessed portions and extended grooved portions, the arrangement being such that when the sections are correctly assembled the recesses define a chamber having inner surfaces for receiving a sample of molten metal, said inner surfaces having a multitude of exposed minute pores, and means substantially filling said pores by treating the inner surfaces with an extremely hot steam whereby to substantially prevent a sample obtained from adhering to said inner surfaces.

5. A device for receiving a sample of molten metal, said device comprising a pair of mating sections of which at least one of said sections is molded from a powdered metal material and has an enlarged recessed portion and an extended grooved portion, means securing said sections together whereby said recessed portion and said grooved portion in combination with the other section define a chamber and a tubular formation, tube means disposed in said tubular formation for receiving molten metal for flow into the chamber, said chamber having inner surfaces interrupted by a multiplicity of open pores which are substantially filled by steam treating said sections whereby to facilitate release of a solid sample obtained in said chamber.

6. In a section of a molded powdered metal constituting a component of a device for receiving a sample of molten metal and said section is provided with a recess for receiving a sample of molten metal and said recess has a surface provided with a plurality of minute pores, the improvement which comprises steam treating said section to substantially fill said pores whereby to substantially prevent a sample obtained from sticking to said surface.

7. A device having internal molded powdered metal porous surfaces defining a chamber for receiving a sample of molten material, said surfaces being steam treated to render them non-porous in a manner whereby a sample formed in the chamber is uncontaminated and may be readily released therefrom.

8. In a device molded from powdered metal having internal porous surfaces defining a chamber for receiving a sample of molten metal, the improvement which comprises subjecting said surfaces to extremely hot steam to form an oxide filling said pores.

9. A method for conditioning a porous structure which is made of molded powdered metal material and provided with internal porous surfaces defining a chamber for receiving a sample of molten metal which comprises subjecting the structure to steam for a period of time sufficient to substantially reduce the porosity of said internal surfaces whereby a solid sample when obtained in said chamber will have uncontaminated smooth surfaces for analysis.

10. The method defined in claim 9, in which the temperature of the steam is within a range of between 550° and 1300° and the time factor is between 4 to 6 hours.

11. A method for conditioning a porous structure which is made from molded powdered metal and provided with internal porous surfaces defining a chamber for receiving a sample of molten metal, which comprises subjecting the structure to steam for a period of time sufficient to cause oxide from the porous structure to substantially fill the pores whereby to facilitate release of a sample obtained from said chamber.

12. The method defined in claim 11, in which the temperature of the steam is within a range of between 550° and 1300° and the time factor is between 4 and 6 hours.

13. In a section of molded powdered metal constituting a component adapted for complementary cooperation with another component to form a chamber for receiving a sample of molten metal and said section has an inner surface provided with a plurality of minute pores, the improvement which comprises steam treating said inner surface to substantially fill said pores whereby to substantially prevent a sample obtained from sticking to said surface.

* * * * *